United States Patent
Ellwart et al.

[11] Patent Number: 5,916,449
[45] Date of Patent: Jun. 29, 1999

[54] METHOD AND ARRANGEMENT FOR MONITORING A SEPARATING LIQUID STREAM

[75] Inventors: Joachim Ellwart, Munich; Ingolf Karls, Feldkirchen, both of Germany

[73] Assignee: Siemens Aktiengesellschaft, Munich, Germany

[21] Appl. No.: 08/754,036

[22] Filed: Dec. 3, 1996

[30] Foreign Application Priority Data

Dec. 28, 1995 [DE] Germany ............... 195 49 015

[51] Int. Cl.⁶ .............. B01D 17/12; B07C 5/02; G06K 9/00; G01N 21/00
[52] U.S. Cl. ............. 210/745; 209/3.2; 209/576; 209/906; 356/410; 382/133; 422/82.05; 436/164
[58] Field of Search ............. 210/94, 745; 422/82.05, 422/82.08, 73, 105; 436/63, 164, 172; 356/39, 72, 73; 382/128, 129, 133, 134, 173, 180; 209/3.1, 3.2, 3.3, 579, 906, 576, 577

[56] References Cited

U.S. PATENT DOCUMENTS

| | | | |
|---|---|---|---|
| 4,317,520 | 3/1982 | Lombardo et al. | 209/3.1 |
| 4,361,400 | 11/1982 | Gray et al. | |
| 4,487,320 | 12/1984 | Auer | 209/3.1 |
| 4,691,829 | 9/1987 | Auer | 209/3.1 |
| 5,594,808 | 1/1997 | Shen et al. | 382/134 |
| 5,602,039 | 2/1997 | Van Den Engh et al. | 422/82.05 |
| 5,643,796 | 7/1997 | Van Den Engh et al. | 209/3.2 |
| 5,700,692 | 12/1997 | Sweet | 436/164 |

FOREIGN PATENT DOCUMENTS

| | | |
|---|---|---|
| 0 025 296 A2 | 3/1981 | European Pat. Off. |
| 27 09 698 | 9/1978 | Germany. |
| 37 05 876 A1 | 4/1988 | Germany. |
| 44 26 490 A1 | 2/1995 | Germany. |
| 1 589 627 | 5/1981 | United Kingdom. |
| WO 96/12172 | 4/1996 | WIPO. |

OTHER PUBLICATIONS

Herzenberg L.A., Sweet, R.G., Herzenberg, L.A., "Fluorescence–activated cell sorting", Sci Amer 234(3): 108, Mar. 1976, pp. 108–117.

*Primary Examiner*—Joseph W. Drodge
*Attorney, Agent, or Firm*—Hill & Simpson

[57] ABSTRACT

A method and an arrangement by which separating liquid streams, such as occur for example in cell sorters, are monitored automatically. An image of the separating liquid streams is recorded and the position of a separation point at which the drops separate from a column of liquid is found using image analysis methods. Various solution possibilities are indicated for the suitable preparation of the image information for easier processing.

18 Claims, 4 Drawing Sheets

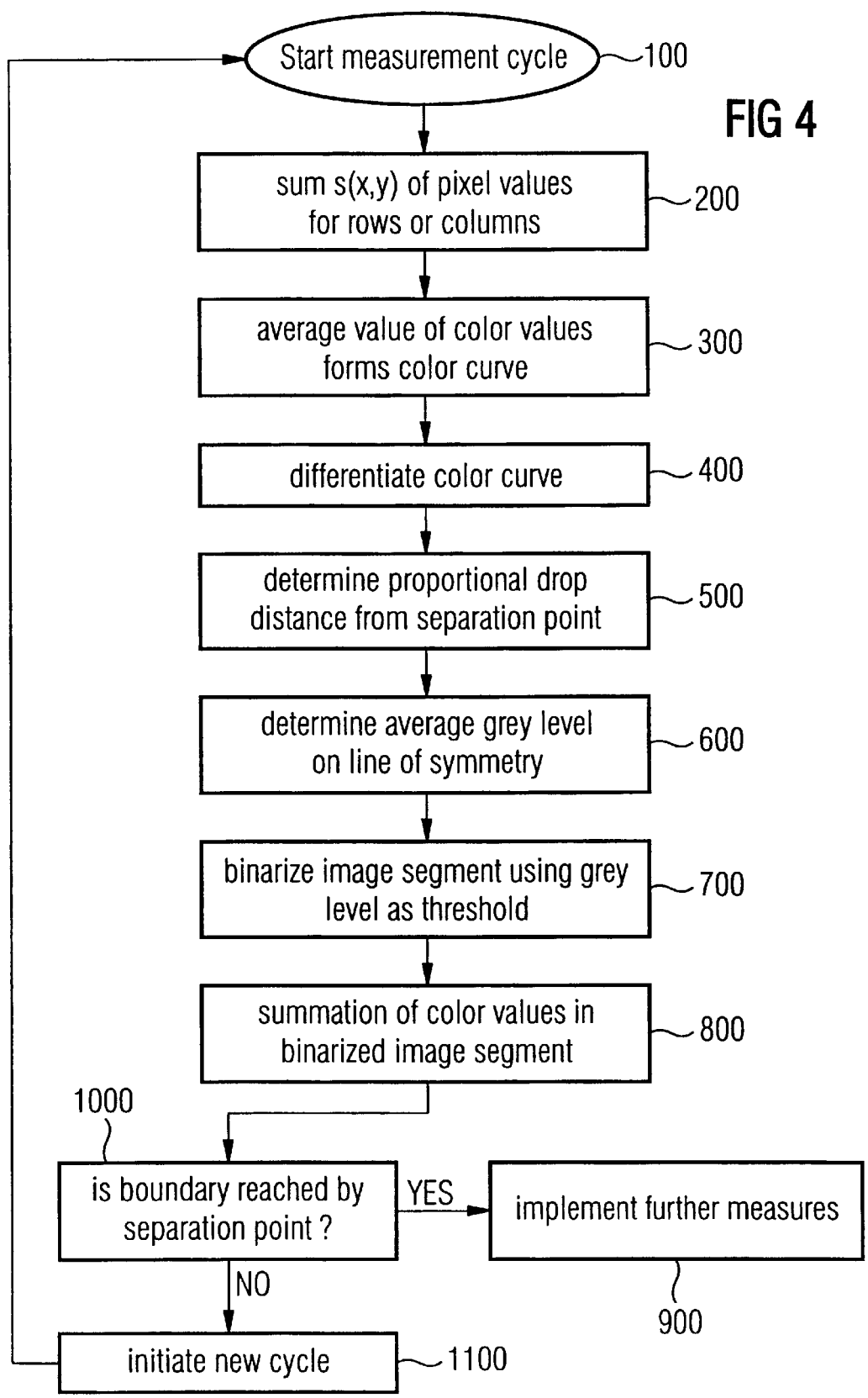

METHOD AND ARRANGEMENT FOR MONITORING A SEPARATING LIQUID STREAM

In general terms the present invention is an arrangement for monitoring a separating liquid stream. Detection means are provided for detection of a variable position of a separation point at which individual drops separate from a column of liquid. Evaluation means are provided for evaluation of the detected position of the separation point in dependence on at least one predetermined position boundary value, by comparing the detected position with the at least one position boundary value. An acting means is provided that is set into action upon the exceeding or, respectively, undershooting of the at least one position boundary value.

The present invention is also a method for monitoring a separating liquid stream. There is acquired the image of a separation point at which individual drops separate from a column of liquid. The position of the separation point in the image is determined by image analysis. The determined position of the separation point is compared with at least one boundary value for the position. A measure is introduced dependent on whether the boundary value is exceeded or, respectively, undershot.

A particular advantage of the inventive arrangement is that it adapts to the position of the separation point, and ensures through suitable evaluation means that the separation point cannot vary its position beyond a boundary value that can be set. If this should nonetheless occur, an acting means is advantageously automatically set into action.

It is particularly advantageous that in the inventive arrangement the position of the separation point is monitored by means of a camera, since still images can easily be produced therefrom, thus providing more time for the evaluation of the position of the separation point.

It is particularly advantageous that the evaluation in the inventive arrangement is carried out by a computer, since if it is determined that the boundary value is exceeded, this computer can set the acting means into action practically without time delay, by means of a suitable interface.

A decisive advantage of the method is that no personnel are tied up by observation.

It is particularly advantageous that the evaluation of the stored camera image can be carried out using the existing pixel information, since separating liquid streams usually have fairly simple basic geometrical structures. In such streams the image information content can be reduced to the essential through suitable measures, thereby essentially simplifying the evaluation expense by the computer. The pixel structure, that is, the coordinate-type construction of the screen in the form of rows and columns, can be used to particular advantage for this purpose. This evaluation can be carried out in a particularly simple fashion if the computer has a frame grabber in which the image is completely stored in the memory, so that separate access to the color information of individual image points can take place for their processing.

A particular advantage of the inventive arrangement is that in case of alarm the process is automatically interrupted, since a human being cannot react so quickly. In the method of the type named, it is necessary to constantly observe the separation point for hours and to react quickly if necessary if the separation point is displaced, since otherwise the entire separation process has to be repeated. Due to the long human reaction time, in case of a disturbance pure fractions practically cannot be obtained. The method is thus advantageously constructed that upon disturbances the sorting process can be interrupted almost without delay.

It is advantageous that in the inventive arrangement acting means are provided in the form of an alarm device in order to indicate irregularities in the separating liquid streams.

It is particularly advantageous that in the inventive arrangement there is provided as an acting means a readjustment of the position of the separation point by an actuator, since it is often the case that an automatic readjustment is more difficult than an interruption of the process, the triggering of an alarm and the correction of the external parameters by an operator.

It is particularly advantageous that the inventive arrangement is used in a cell sorter, since until now very time-consuming observations by a human observer have been required for the monitoring of the separation process.

It is particularly advantageous that in the inventive method the position of a separation point, at which individual drops separate off from a liquid stream, is monitored, and the position thereof is determined using an image analysis of the recorded image, since this position can be monitored well and an exceeding of a predefined position boundary value leads to defined acting conditions for the inventive method.

It is particularly advantageous that in the inventive method the direction of the liquid stream in the recorded image is determined by analyzing the image row by row or, respectively, column by column. The inventive method thereby advantageously exploits the fact that a liquid stream essentially presents a straight line on the screen, and that the direction in which the stream runs can be discovered precisely through line-oriented or, respectively, column-oriented image analysis of the coloration of the individual pixel values. In addition, the inventive method advantageously makes use of the fact that the stream enters continuously at one side of the image and that afterwards, after separation of the individual drops from the point of separation, interruptions are present in the stream. The position of the separation point can thus be precisely detected by examining the color values of the individual pixels along the axis of symmetry of the stream. At the first significant color change, the position of the separation point in the image has been found, and the coordinates of these pixel values represent in the computer the position of the separation point. At the start of the inventive method, the separating liquid stream can be normed precisely to these values, and the position boundary value of the separation point can thus be correspondingly defined relative thereto.

It is particularly advantageous that in the inventive method a small evaluation window is formed that is arranged symmetrically around the separation point, since in this way the image analysis expense can be essentially reduced.

It is particularly advantageous that the image information of the recorded momentary image is discretized by means of two color values, which are found, for example, by the row-by-row or column-by-column averaging. All color values beneath the minimum are thereby for example selected black and all color values above the minimum are for example selected white, so that in this way the image analysis expense can be additionally reduced. As a result separating liquid streams with a high drop sequence can be monitored, or, respectively, a less powerful computer can be used for the application of the method.

BRIEF DESCRIPTION OF THE DRAWINGS

The features of the present invention which are believed to be novel, are set forth with particularity in the appended claims. The invention, together with further objects and advantages, may best be understood by reference to the following description taken in conjunction with the accompanying drawings, in the several Figures of which like reference numerals identify like elements, and in which:

FIG. 4 is a flow diagram of the inventive method.

DESCRIPTION OF THE PREFERRED EMBODIMENTS

Figure 1:
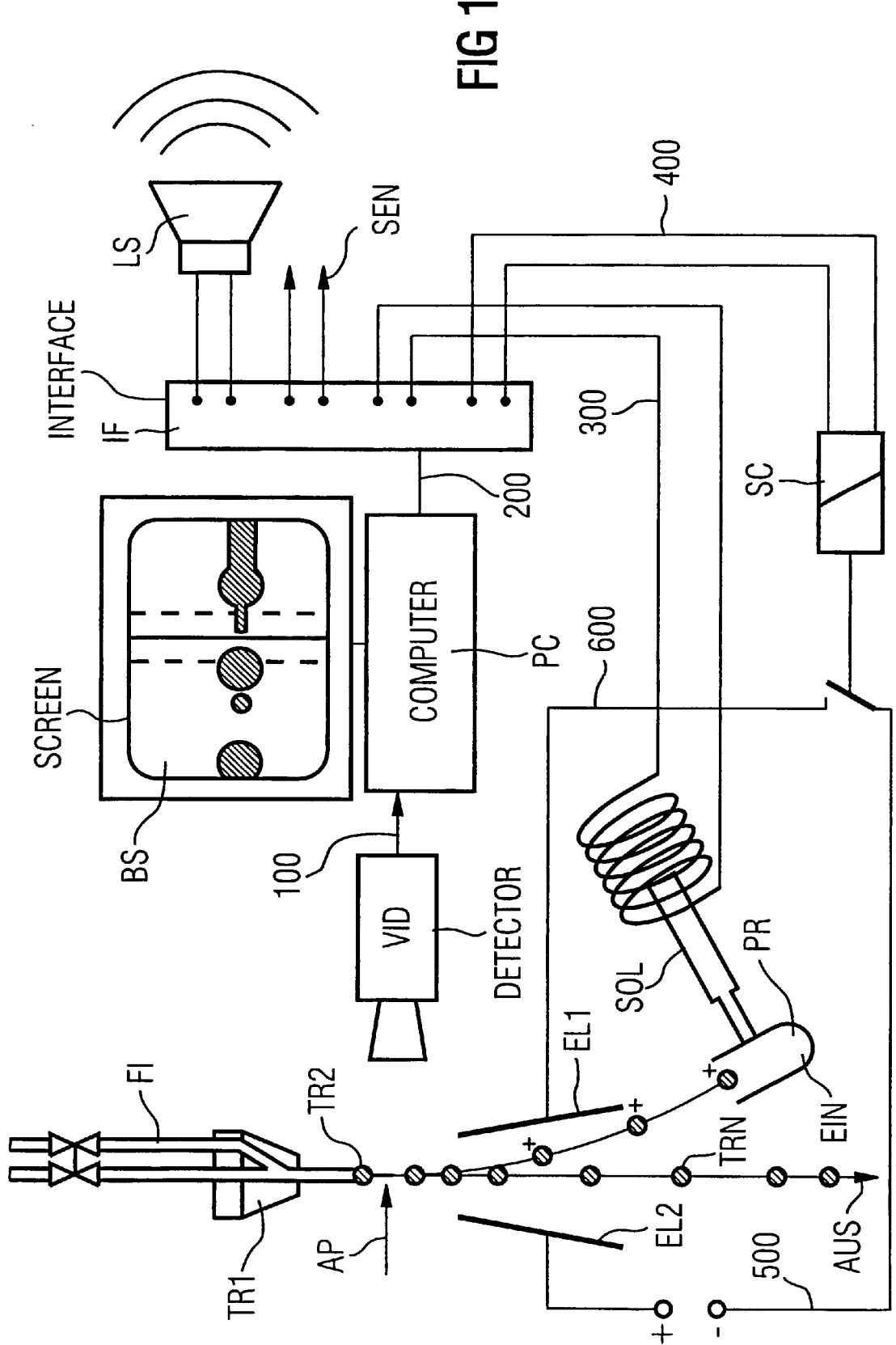
FIG. 1 depicts an example of the application of the inventive arrangement in a cell sorter.

FIG. 1 shows a highly schematized image of the application of an inventive arrangement in a cell sorter. Particular components of the arrangement that are to be noted consist in a free liquid stream FL, from which a drop TR1 separates and which forms a separation point AP. The second drop TR2 is the first drop that has separated itself from the separation point AP. This process is observed by means of a camera or another detector VID, which forward their signals to a processing unit via a line 100. This processing unit is designated PC and can for example be a computer or other hardware that serves to evaluate the signal of the detector. Additional drops are also shown, numbered up to TRN.

In a cell sorter, individual biological cells or other particles in an electrically conductive suspension are characterized in a suitable way through optical or electrical means and sorted from one another according to their characteristics. After exiting from a nozzle, they are located successively in the liquid stream FL. The drops separating themselves from the liquid stream FL are guided through an electrical field between the electrodes EL1 and EL2, so that electrically charged particles are deflected into a sampling tube PR. Upon separation from the liquid stream FL, the drops are charged by the momentary electrical charge of the liquid stream FL. The charge of the liquid stream is oriented according to the sorting criteria determined by the optical or, respectively, electrical characteristics of the particles to be sorted.

The evaluation means PC are here connected for example with a display screen BS, on which the separation point AP is shown. In the evaluation means PC, which can be for example a personal computer, it is evaluated to what extent the separation edge or the separation point AP are displaced. For this purpose, at first for example a correct separating liquid stream is set by a human operator, which essentially separates in a temporally and spatially stable fashion from the separation point AP. The overall arrangement is for example normed to this, and a safety distance is determined as a position boundary for the separation point. If now during the separation process the separation point AP moves, this is shown on the screen, and, upon exceeding of a previously determined boundary value, an acting means is actuated, via for example a line 200 to an interface IF. This acting means is for example a loudspeaker LS, a radio alarm SEN, or magnetic valves that interrupt the liquid stream FL. An additional acting means can for example be a solenoid SOL, which, by means of an electromagnet actuated via the lines 300, removes the sample glass PR from the sample stream of direction EIN.

It is to be noted that the version shown here of a cell sorter is only an example for the application of an inventive arrangement. The processes are shown in highly schematized form, and other detectors VID are also possible throughout. Such detectors can be for example light barriers, ultrasound or capacitative sensors. Through these detection means, it need only be ensured that the position of a separation point AP can be detected with sufficient precision. In cell sorters, cameras are preferably to be used, since these are already provided to enable the human operator to observe the separation point on a screen BS. In the invention, the screen content is thus preferably evaluated in the evaluation means PC, using an image analysis. For this purpose, momentary exposures of the separating liquid stream are for example produced, and the position of the separation point AP is found according to the inventive method by means of row-by-row and column-by-column analyses of the individual pixel color values. Through suitable measures, such as for example the discretization of the pixel color values into at least two values, which amounts to a contrast amplification, the computing expense within the evaluation means PC is also simplified. It is thereby possible to use less powerful processors, or, respectively, a higher drop frequency. According to the desired resolution, the inventive method can be executed in real time, or only individual drops can be imaged stroboscopically with the momentary exposures, in for example a frame grabber in the PC, so that for example the separation point is photographed only at every tenth drop occurrence. For the selection of this resolution, the costs and the desired resolution in the application of the inventive method and the inventive arrangement are significant, since with increasing resolution the computing expense increases, and the costs for the evaluating means thereby also increase.

Figure 2:
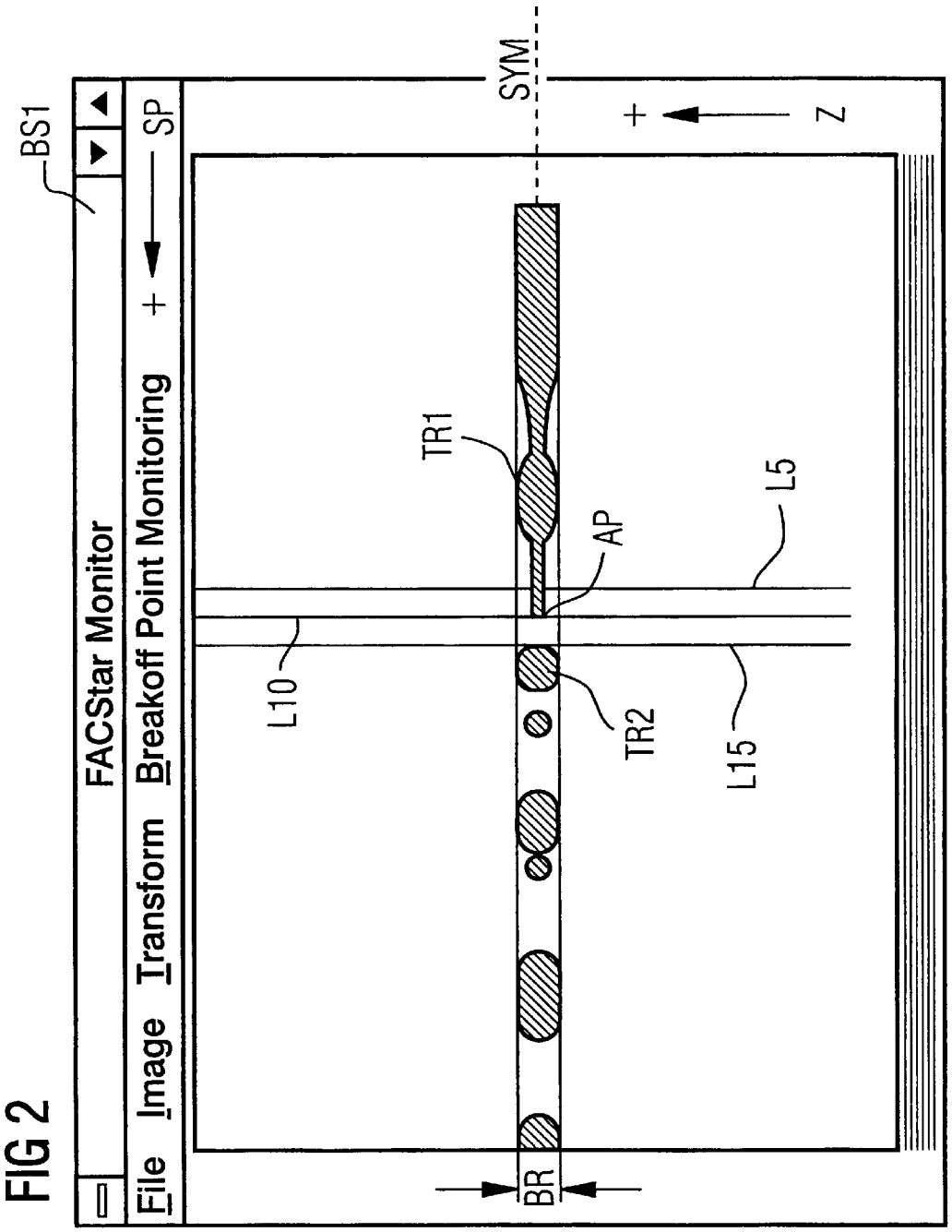
FIG. 2 and FIG. 3 show a momentary image of a photographed separating liquid stream.

FIG. 2 shows an example of a screen segment of the screen BS from FIG. 1. The screen is for example a raster screen divided into rows Z and columns SP. The liquid stream enters the screen BS1, for example, here from the right along an axis of symmetry SYM in the positive column direction SP. The separation point AP is here marked by means of a line L10. The drop TR1 is also shown again here as in FIG. 1. Position boundary values for the separation point, L15 and L5 can be seen clearly on the image BS1. These position boundary values are preferably chosen so that they comprise a distance proportional to the drop distance from the separation point AP. Since a separation process is essentially a stream-shaped process along the axis of symmetry SYM, with the inventive method the possibility advantageously suggests itself of examining only image contents along this stream. For this purpose, a region of width BR is for example selected around the axis of symmetry. This region can be seen here in the positive column direction as a white strip.

The inventive method for detection of the separation point by means of image analysis preferably proceeds as follows.

In order to find the position of the line of symmetry, the position of the greatest blackness (optical density) or, in an inverse image, of the greatest whiteness per column or per row is sought either row by row or column by column according to the curve of the liquid stream over the image. The symmetry characteristic of the liquid stream is thereby exploited, since it is known that a drop has a small extension in relation to the overall screen content, and that the stream runs along an axis of symmetry. Through the analysis of the individual row or, respectively, column contents, a sequence of pixel coordinates is obtained that comprise an increased blackness or an increased whiteness. Given several pixel values along a row, or, respectively, column, the minimum or, respectively, the most significant pixel value can be found by averaging the individual coordinate values of the pixels.

In this way, different points are found along the axis of symmetry that indicate the curve of the liquid stream, and in particular the curve of the symmetry axis SYM. For the further execution of the inventive method, the color values of the individual screen pixels can preferably be discretized along the axis of symmetry. In order to reduce the analysis expense in the execution of the inventive method, the individual pixels are preferably assigned only two colors, for example, black and white. For the discretization of these two color values, that is, in order to find a boundary that distinguishes white from black, for example all color values are integrated along the axis of symmetry, and are divided by the number of rows or, respectively, columns, so that exactly one average value is obtained for all the color values. As a result, this average value then serves for example as a boundary for distinguishing between black and white. All color values that lie beneath the average value are thereby assigned the value black, and all those lying above the average value are for example assigned the value white. The same procedure can also be carried out for the additional simplification of the image information in the respective other direction, thus given rows/column direction and given columns/row direction. After the drop stream has been prepared in this way, the separation point AP can be sought using the inventive method. For this purpose it is presupposed that the direction of the entry of the stream of liquid into the image is known. Starting from this edge of the image, the pixel coordinates at which the color value changes are then sought, using the inventive method, along the axis of symmetry. These pixel coordinates represent precisely the location of the separation point AP. Starting from this current pixel value, for example the position boundary value for the separation point L15 and L5 is preferably defined at a distance proportional to the drop distance from the separation point. Determinate pixel coordinates are connected with these position boundary values. The inventive method can now be carried out cyclically, and the separation point is always found by means of the inventive procedure. If the separation point AP reaches one of the boundary values L15 or L5, that is, the coordinate value of the separation point AP takes on either L5 or L15, then suitable measures can for example be introduced for the correction of the separation point AP. With a measure of this sort, the process can for example be interrupted immediately, and a human operator can be called by means of an alarm, or suitable automatic means can be activated in order to guide the separation point back to the correct position.

Figure 3:
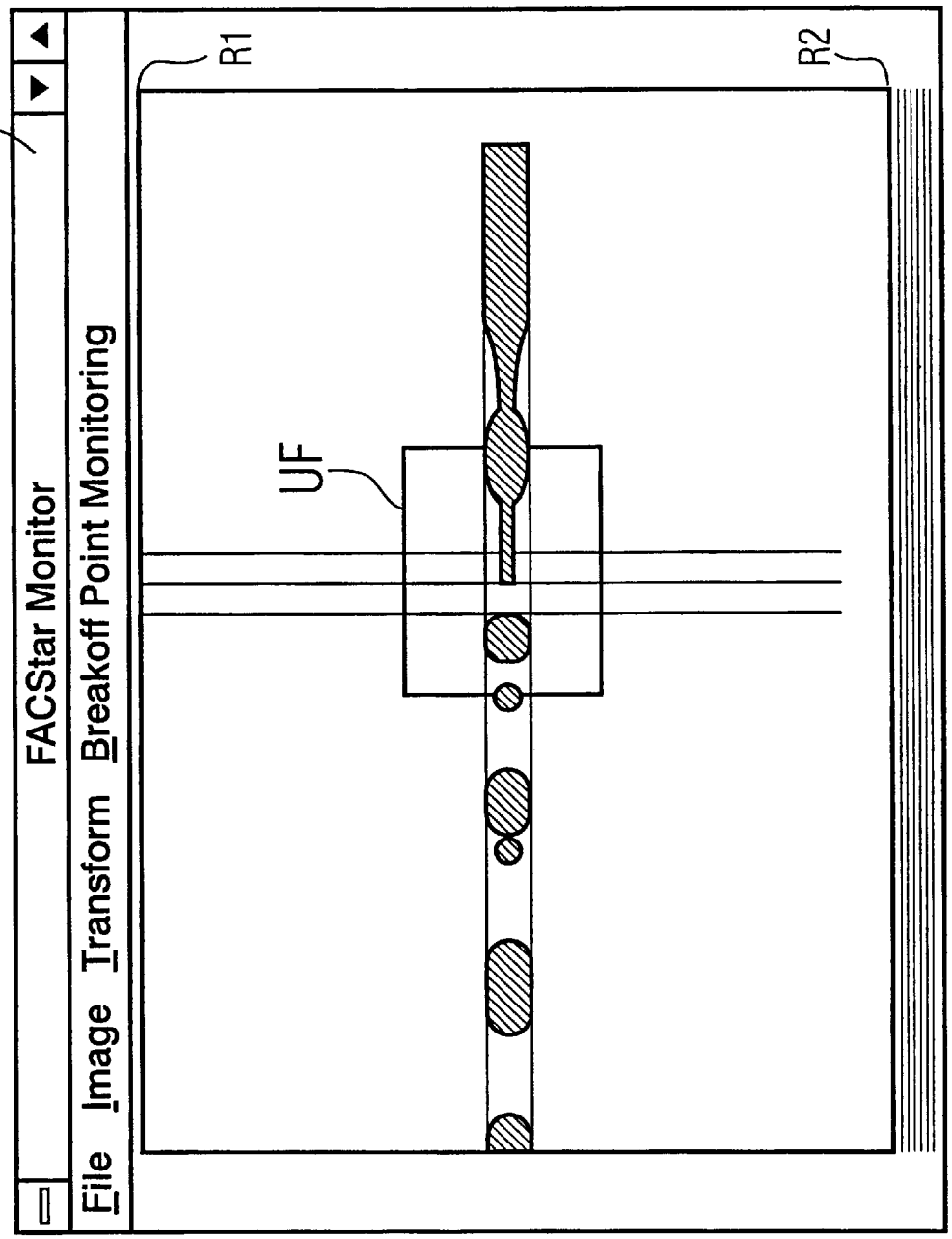

FIG. 3 likewise shows the screen segment BS1 shown in FIG. 2. FIG. 3 shows a monitoring window UF that can be defined around the separation point AP after the separation point AP has been found as described in FIG. 2. As can be seen, as a surface the monitoring window UF takes up a considerably smaller part than the overall screen, for example, 5% of the screen content, which means that the analysis according to the inventive method can be carried out essentially more quickly and in a shorter time without an accompanying loss of information. It is thus assumed that the inventive method is carried out for example only inside the monitoring window UF. Boundaries R1 and R2 can be further provided, which represent the lower and the upper edge of the screen, in order thereby to allow a drift of the axis of symmetry SYM, and to introduce suitable measures for the recentering of the axis of symmetry SYM only if this axis exceeds these boundary values R1 and R2.

FIG. 4 shows an example of a flow diagram for a cyclically executed inventive method. In step 100 of the inventive method, the measurement cycle is for example started. In step 200, the sum S(x,y) of the pixel color values of the columns or, respectively, rows in the image is for example calculated. In step 300, the average value of the color values found is for example formed, in order to enable the discrimination of the individual pixel color values into two colors. In this way, a color curve is obtained transversely over the screen in the horizontal direction. In step 400, this color curve is differentiated, and the point of the minimum or, respectively, the maximum is thereby found. This maximal or minimal crossing represents the position of the symmetry line SYM. Subsequently, in a step 500 the proportional drop distance from the separation point is for example determined. This corresponds to the channel width BR shown in FIG. 2 and FIG. 3. This channel width results from the color curve through the formation of the difference between the maximum or, respectively, minimum and the zero crossing of the function. This distance represents a useful measure for the limitation of the observation space in the image analysis. In addition, it indicates a good measure for the determination of the position boundary values for the separation point. This distance measure is used for example for the determination of the boundaries L5 and L15. These boundaries are chosen so that they have a distance from the separation point that is proportional to the drop distance.

In a step 600, the average grey value on the line of symmetry is for example found, by adding together the individual pixel color values and dividing by the number of columns or, respectively, rows. In a further step 700, the binarization of the image segment takes place. The average grey value serves as the threshold value for the binarization. In a step 800, the calculation of the sums of the color values is carried out in the binarized image segment. For this purpose, by means of the inventive method the sum formation is carried out outward from the edge of the image at which the continuous liquid stream, that is, the liquid column, enters the image. The separation point is found when a column or a line occurs that contributes nothing more to the sum. Preferably, the column-by-column or, respectively, row-by-row alteration of the sums can be observed, that is, the sum function can be differentiated, and the location of the separation point is found upon the occurrence of a first minimum. In a step 1000 of the inventive method, it is then checked whether the position boundary L15 or L5 was reached by the position of the separation point. If yes, in a step 900 a suitable measure is introduced. If no, in a step 1100 a new measurement cycle is initiated.

The invention is not limited to the particular details of the method and apparatus depicted and other modifications and applications are contemplated. Certain other changes may be made in the above described method and apparatus without departing from the true spirit and scope of the invention herein involved. It is intended, therefore, that the subject matter in the above depiction shall be interpreted as illustrative and not in a limiting sense.

What is claimed is:

1. An arrangement for monitoring a separating liquid stream, comprising:
 a detection device operable for detection of a variable position of a separation point at which individual drops separate from a column of liquid by detecting a pixel image;
 an evaluation device operable for evaluation of the detected position of the separation point with respect to at least one predetermined position boundary value by row or column analysis of the image, the evaluation device comparing the detected position with the at least one position boundary value; and an acting device that is set into action upon the detected position deviating more than a predetermined distance from a predetermined reference position as determined by the evaluation device.

2. The arrangement according to claim 1, wherein the detection device is a monitoring camera that is connected to and that operates together with image storage devices for storing at least one momentary photograph of the separation point.

3. The arrangement according to claim 1, wherein the evaluation device is a computer.

4. The arrangement according to claim 3, wherein the computer has a graphics card with a frame grabber, and wherein the computer is structured such that a graphic evaluation of each of the at least one position boundary value is based on pixel information stored as a momentary image, the position boundary value being predetermined in the form of pixel coordinate values.

5. The arrangement according to claim 1, wherein the acting device is an alarm device.

6. The arrangement according to claim 1, wherein the acting device automatically interrupts the liquid stream.

7. The arrangement according to claim 1, wherein the acting device is an actuator that readjusts the separation point.

8. The arrangement according to claim 1, wherein the separation point of the liquid stream in a cell sorter is monitored.

9. A method for monitoring a separating liquid stream, comprising the steps of:
   acquiring a pixel image of a separation point at which individual drops separate from a column of liquid;
   determining a position of the separation point in the image by row or column analysis of the image, thereof;
   comparing the determined position of the separation point to at least one boundary value for the position; and
   introducing a measure dependent on the determined position deviating more than a predetermined distance from a predetermined reference point based on said comparison.

10. The method according to claim 9, wherein the method further comprises:
   determining drop direction for the image analysis by examining pixel information of the image row by row or, alternatively, column by column for locations of higher coloration, and connecting these locations by a straight line after averaging, which line forms a line of symmetry of a drop stream that is formed by the individual drops; and
   determining a location of lower coloration along the line of symmetry, beginning at a known side of entry of the column of liquid into the image and continuing to the other side of the image, said location of lower coloration being a position of the separation point in the image.

11. The method according to claim 10, wherein an extreme value of color values of the pixels is determined in a row and/or column direction, and wherein only two discrete values are allocated to the color values of the pixels, used for undershooting thereof in allocation of extreme values, so that all values that exceed the extreme value receive one color value, and all other values in the respective row and/or column receive the other color value.

12. The method according to claim 9, wherein a search window is defined around the separation edge, said window being substantially smaller than the image.

13. The method according to claim 9, wherein the measure is an interruption of the liquid stream.

14. The method according to claim 9, wherein the measure is the removing of a small sorting tube from a stream of the individual droplets.

15. An arrangement for monitoring a separating liquid stream, comprising:
   a detection device operable for detection of a variable position of a separation point at which individual drops separate from a column of liquid, the detection device being a monitoring camera that is connected to and that operates together with image storage devices for storing at least one momentary photograph of the separation point;
   a computer operable for evaluation of the detected position of the separation point in dependence on at least one predetermined position boundary value, the computer comparing the detected position with the at least one position boundary value, the computer being structured such that a graphic evaluation of the position boundary value is based on row or column analysis of pixel information stored as a momentary image, the position boundary value being predetermined in the form of pixel coordinate values;
   an alarm device that is activated by a result of the comparing that indicates the detected position deviating more than a predetermined distance from a predetermined reference position as determined by the computer.

16. The arrangement according to claim 15, wherein said result of the comparison effects automatic interruption of the liquid stream.

17. The arrangement according to claim 15, wherein said result of the comparison activates an actuator that readjusts the separation point.

18. The arrangement according to claim 15, wherein the separation point of the liquid stream in a cell sorter is monitored.

* * * * *